United States Patent [19]

Andersson et al.

[11] Patent Number: 6,104,294
[45] Date of Patent: Aug. 15, 2000

[54] ACTIVITY MEASUREMENT

[75] Inventors: Peter Andersson, Enskede; Jianning Li, Ronninge, both of Sweden

[73] Assignee: Alfa Laval Agri AB, Tumba, Sweden

[21] Appl. No.: 09/101,064

[22] PCT Filed: Dec. 30, 1996

[86] PCT No.: PCT/SE96/01762

§ 371 Date: Sep. 14, 1998

§ 102(e) Date: Sep. 14, 1998

[87] PCT Pub. No.: WO97/24027

PCT Pub. Date: Jul. 10, 1997

[30] Foreign Application Priority Data

Dec. 29, 1995 [SE] Sweden .................................. 9504707

[51] Int. Cl.$^7$ ................................................ G08B 23/00
[52] U.S. Cl. ........................... 340/573.3; 340/573.4; 340/825; 340/539; 340/531; 340/669; 119/712; 119/719; 600/549
[58] Field of Search ........................ 340/573.3, 825.54, 340/539, 573.4, 531, 669, 689, 687, 686.1; 119/712, 719, 14.14, 51.02; 600/549

[56] References Cited

U.S. PATENT DOCUMENTS

| 3,557,758 | 1/1971 | Lack ......................................... 119/51 |
| 4,455,610 | 6/1984 | Rodrian .................................. 364/415 |
| 4,510,495 | 4/1985 | Sigrimis et al. .................... 340/825.54 |
| 4,854,328 | 8/1989 | Pollack .................................... 128/736 |
| 4,865,044 | 9/1989 | Wallace et al. ......................... 128/736 |

FOREIGN PATENT DOCUMENTS

| 2260196 | 4/1993 | European Pat. Off. .......... A61B 5/11 |
| 549081 | 6/1993 | European Pat. Off. ........ A61B 10/00 |
| WO9111678 | 8/1991 | WIPO .............................. G01B 1/16 |
| WO9532616 | 12/1995 | WIPO ........................... A61B 10/00 |

*Primary Examiner*—Daniel J. Wu
*Assistant Examiner*—Tai T. Nguyen
*Attorney, Agent, or Firm*—Hovey, Williams, Timmons & Collins

[57] ABSTRACT

A motion sensor unit (11) is intended to be carried by a domestic animal. The motion sensor unit (11) operates in parallel to and independently of a conventional transponder unit (1). The motion sensor unit (11) contains a motion detector (14) for measuring the activity of the animal by providing electrical pulses when the animal moves. Each hour is subdivided in a number of intervals in each one of which it is determined if the activity has exceeded a certain threshold. If it is the case, a count value is incremented. The count value is then transmitted once each hour and in addition also the count values of all the 23 previous hours. By transmitting repeatedly such information a good safety is obtained in the reception of the information signal, and this information can be used for complicated evaluation processing in a processor (7) or a supplementary personal computer (9).

6 Claims, 5 Drawing Sheets

FIG. 2      Sensor output
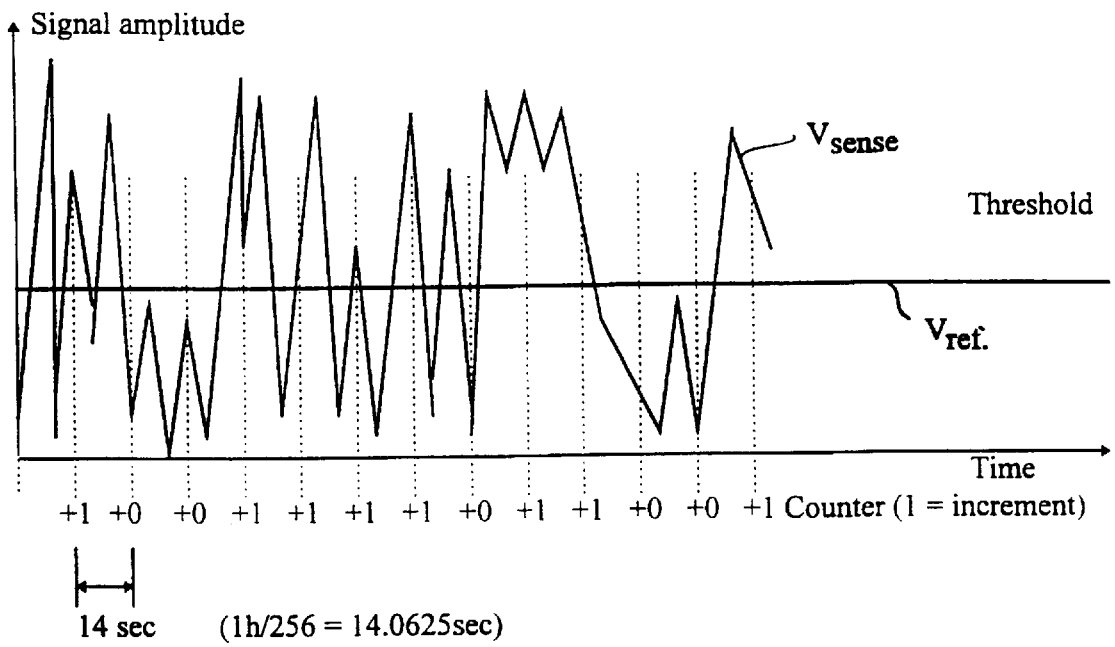
FIG. 3      Counter array.
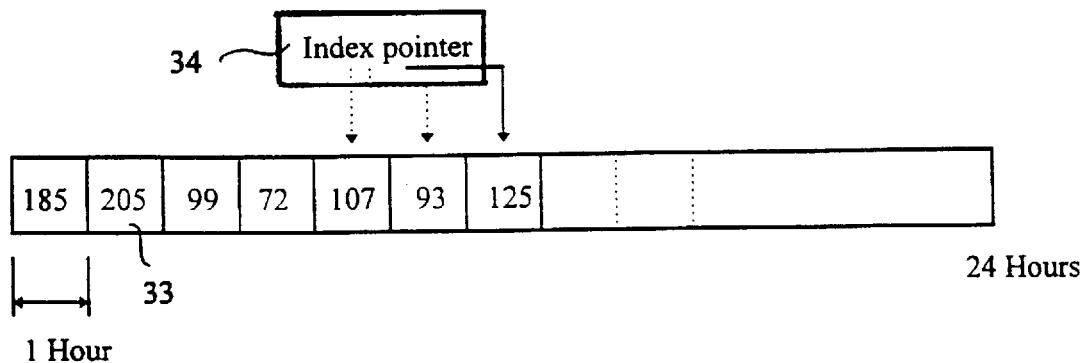
FIG. 4      Transmission block
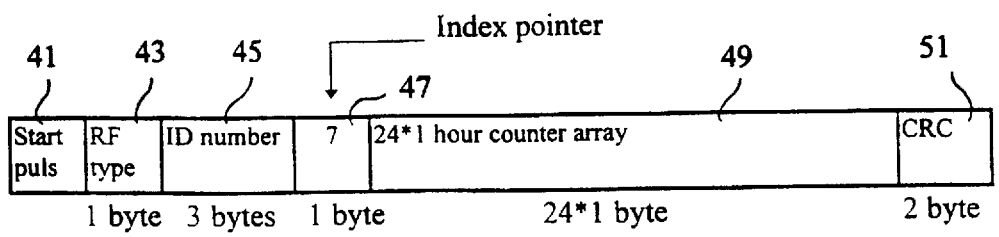

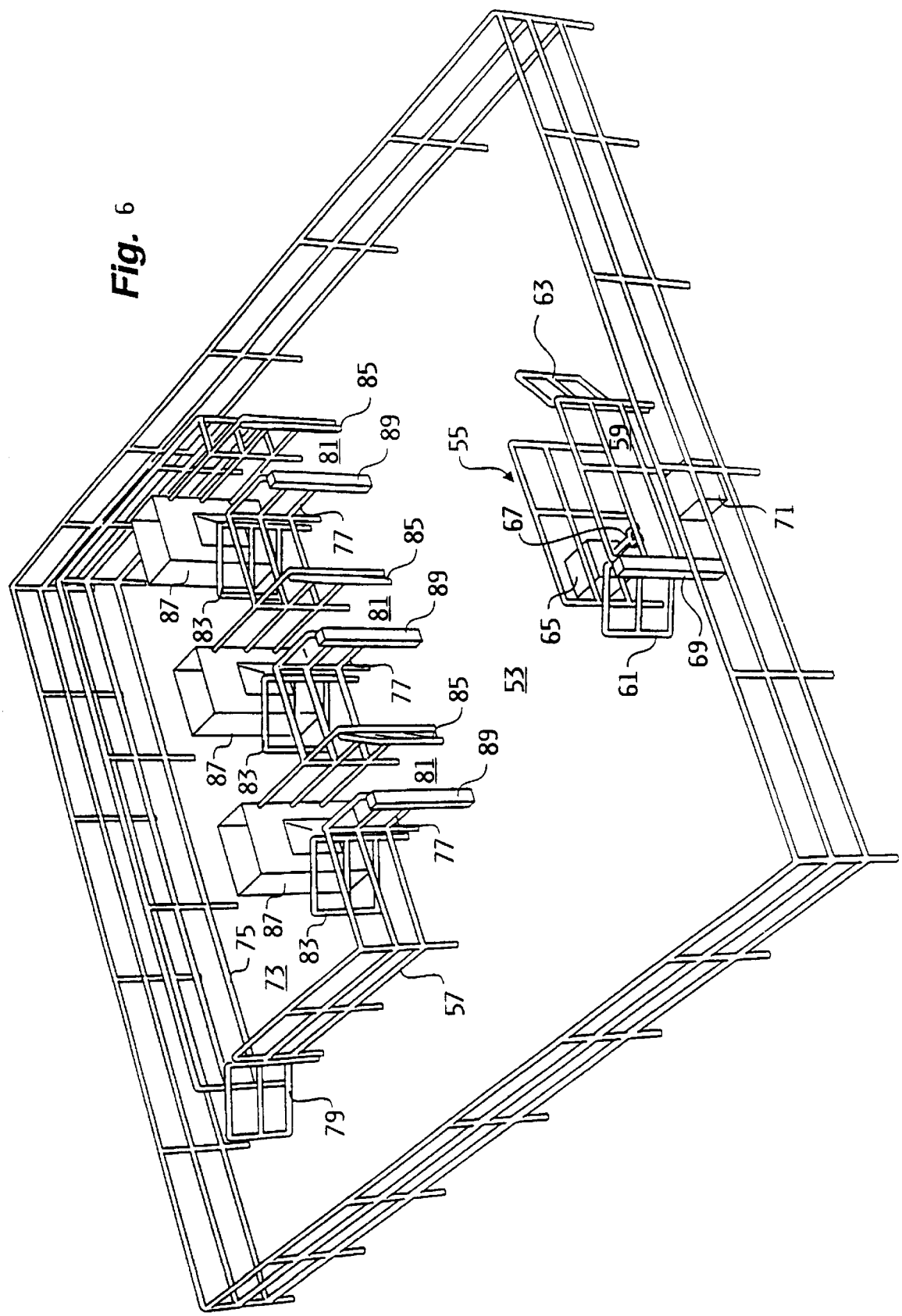

ACTIVITY MEASUREMENT

BACKGROUND OF THE INVENTION

1. Field of the Invention

The present invention relates to a method and a device for measuring the activity of domestic animals comprising an automatic transfer of measurement results to a central evaluation station.

2. Description of the Prior Art

Identification systems for domestic animals comprising a passive transponder unit attached to an animal have been widely used and the constructional details thereof have been elaborated. See e.g. U.S. Pat. Nos. 4,510,495, 4,247,758 and 4,618,861, and the International patent application having publication number WO 91/11678.

In U.S. Pat. No. 4,510,495 a remote passive identification system is disclosed using a transponder responding to signals from a power transmitter. The animal identification and estrus detection system of U.S. Pat. No. 4,247,758 uses a transponder, that is a passive unit, which is interrogated and then transfers information of the number of movements of the animal. In the estrus detection system of U.S. Pat. No. 4,618,861 also a transponder is used, that obtains data from a self-powered motion sensor. Thus these two latter patents rely upon a transponder unit such that the animal estrus information about a particular animal can only be recorded when the animal passes near a transponder reader. For detecting estrus, the motion activity is determined or the fact whether the motion activity of the domestic animal has increased drastically is determined. Information of the result of the determination is communicated together with identification information for identifying the animal.

An estrus detector using such method is also disclosed in the European patent having publication number EP-B1 0 087 015, but here an estrus detection tag is used, that is self-contained having a visual indication and no remote information transfer. Such a visual indication can be missed or not seen during a critical period. A similar self-contained estrus detector is also disclosed in U.S. Pat. No. 4,895,165 but there the general motion activity of the animal is not monitored.

In the European patent application having publication number 0 549 081 measurements of the activity of an animal are made by means of an implanted device powered by an internal electrochemical battery and comprising a motion sensor and a temperature sensor providing signals. The signals can be processed by a processor having a memory in the device to give some characteristic value. This can be made by storing successive measurement signals until a certain number of signals has been collected. Then the stored values are used for determining a characteristic value that is again stored, the used values being eliminated from the memory. Such characteristic values are stored during a time interval and are then transmitted. The length of the time interval can be determined by the time at which the animal is in the direct vicinity of a reception device. For storing successive measurement signals a substantial memory is required drawing a corresponding amount a electric power. The processing of signals inside the device requires a considerable amount of electric energy.

In the published International patent application having publication number WO 95/32616 an electrochemical battery is used as a power source for the transmission of a signal indicating that the motion activity has increased. This design provides advantages such as a larger obtainable range for the transmitted signal. A disadvantage therein is that transmission is made only once and that it is not made sure that the signal is received by a centrally located station, for reasons such as the limited range of the transmitter, the fact that the animal can be at an unsuitable location when the transmission is made, etc. The transmitter of these data can also become non-operative and this condition will not be detected in this prior construction.

SUMMARY OF THE INVENTION

It is an object of the invention to provide a data collection and identification unit that can be used on an animal during a long time period and that transmits collected data safely to a central data processing station.

It is a further object of the invention to provide a motion detector unit for an animal that transmits information that can be used for diagnosing various states of the animal.

These objects are achieved by the invention hereof as more fully described below.

Thus, generally, the animal is provided with some sensor means for monitoring the motion intensity of a domestic animal for detecting and transmitting different motion states of the sensor and thus also of the animal. The sensor is more or less rigidly attached to the animal. The sensor is assumed to be capable of detecting at least two different motion states, a first normal state and a second particular state, for instance some state involving relatively intense or frequent movements. A timer connected to a processor is provided for detecting the rate or frequency of the particular states. In particular the timer and processor are arranged so that at periodically repeated times having time intervals therebetween of a first predetermined length, it is determined whether the animal during the time interval from the next previous time has adopted the second, particular state and that the number of such times corresponding to the second, particular state are counted, when they occur. A transmitter is coupled to the processor for transmitting, at less frequent, periodically repeated times having time intervals therebetween of a second predetermined length that is larger than the first predetermined length, information of the determined rate or frequency to an evaluation station. Such information is in regard of the counted number, i.e. how many times after the previous transmission occasion it has been counted that the second state has been adopted.

The particular feature of only counting states requires very little electric energy, compared to methods where complete measurement signals are stored before internal processing or transmission, compare the cited International patent application WO 91/11678 and European patent application 0 549 081.

During or associated with each transmission to the evaluation station, information can also be transmitted in regard of the counted numbers during several time intervals before the present time.

At the periodically repeated times, when information is transmitted to an evaluation station, identification information is then also advantageously transmitted for identifying the transmitter by the processor and thereby the sensor means and the animal.

The timer means is thus arranged to provide first clock pulses of a first predetermined rate, having time intervals therebetween of a first predetermined length. The timer means also preferably provides second clock pulses of a second predetermined rate that is slower than the first rate, that is the second clock pulses being provided at less frequent, periodically repeated times having time intervals therebetween of a second predetermined length, that are thus larger than the intervals of the first predetermined length.

The processor comprises memory means for storing at least one counted number. Furthermore, it comprises determining means coupled to the sensor means and the timer means for receiving the first clock pulses and for determining, at the reception of each first clock pulse, whether the animal during the time interval from the next previous time, when a first clock pulse was received, has adopted the second, particular state. The determining means are also coupled to the memory means for storing therein the number of such times when the second particular state has been adopted. The processor means has in addition control means coupled to the memory means, the timer means and the transmission means. The control means is arranged to control the transmission means for transmitting, at less frequent, periodically repeated times having time intervals therebetween of a second predetermined length, that is larger than the first predetermined length, information to the evaluation station in regard of the counted number stored in the memory means.

The memory means can further be arranged for storing several counted numbers, and then the determining means are arranged to store counted numbers for at least two, and preferably a multitude of successive time intervals having the second predetermined length. The control means can then be arranged to also transmit, at the periodically repeated times when information is transmitted to the evaluation station, information in regard to the counted numbers during at least two time intervals having the second length, before the present time.

The memory means may also be arranged to store an identification number or identification sequence. When so arranged, the control means are preferably arranged to also transmit, at the periodically repeated times when information is transmitted to the evaluation station, identification information derived from the stored identification sequence for identifying the transmitter and thereby the sensor means and the animal.

BRIEF DESCRIPTION OF THE DRAWINGS

The invention will now be described by way of a non-limiting particular embodiment with reference to the accompanying drawings in which:

FIG. 2 is a diagram where the output of a sensor in an activity measuring device is drawn as a function of time;

FIG. 3 is a picture illustrating the organization of the memory fields for storing counted values in the activity measuring device;

FIG. 4 is a picture illustrating the format of an information block transmitted from the activity measuring device;

FIG. 6 is a perspective view of a corral for freely walking animals in which there is provided a separation device suitable for separating animals which are in certain motion states;

DETAILED DESCRIPTION

Figure 1:
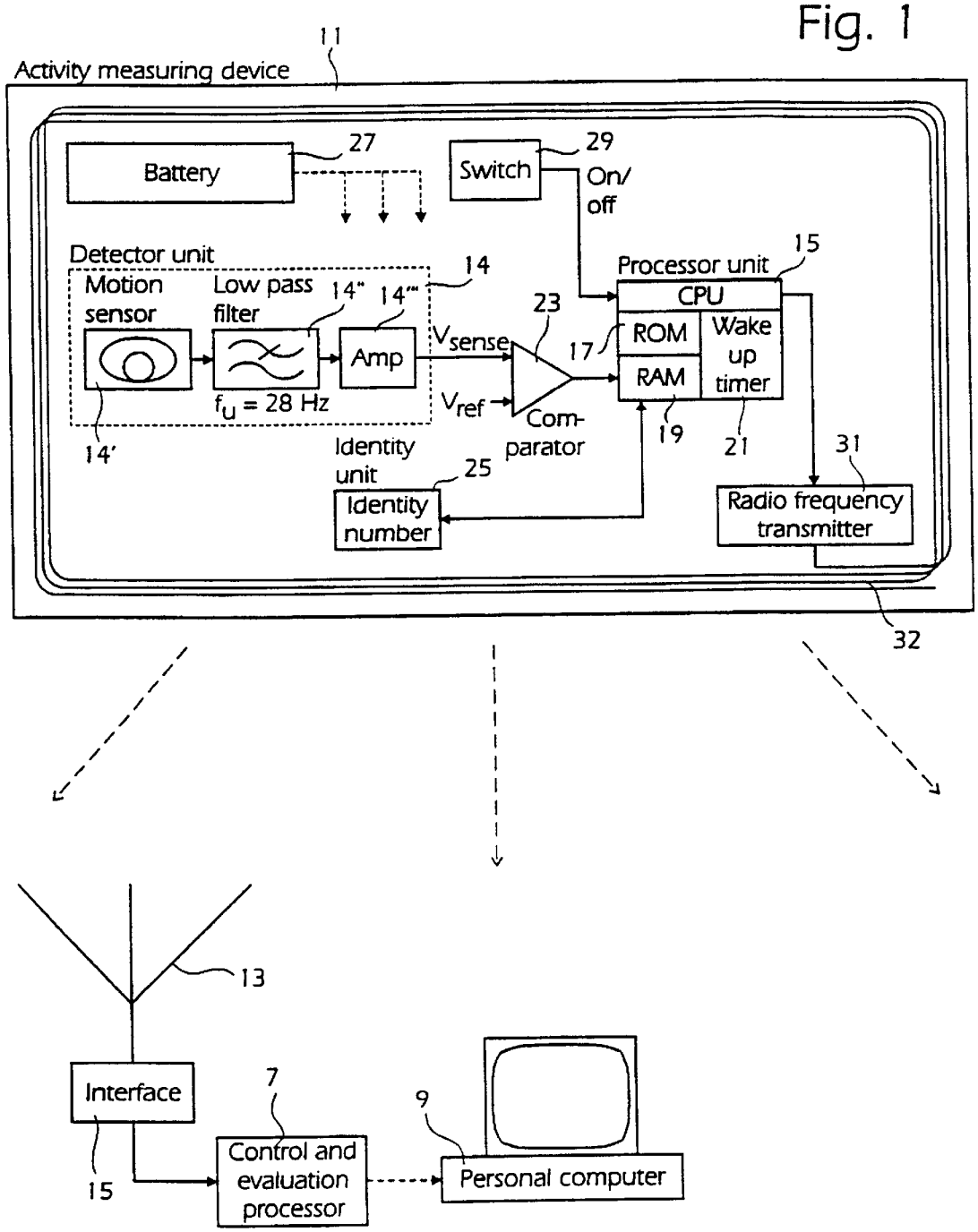
FIG. 1 is a schematic block diagram illustrating an installation for automatic identification and activity measurement of an animal.

In FIG. 1 a block diagram is shown illustrating an installation for identification and activity measurement of an animal, e.g. a domestic animal such as a dairy cow. In an evaluation station, that can be stationary, a processor unit 7 is located, which can possibly be coupled to a personal computer indicated at 9. The installation further comprises a motion sensor unit or activity measuring device 11 to be worn or carried by the animal. The activity measuring device 11 is arranged for transmitting information to the evaluation station. The measuring device 11 emits radio frequency signals, that are to be received by an antenna 13 connected to an interface 15. The interface 15 decodes the received information and transmits it to the processor 7, where the information is further processed, such as for generating some kind of alarm.

The motion sensor unit 11 comprises as its core part a motion detector unit 14 which can be the kind of electromagnetic sensor described in our previous International patent application PCT/SE95/00630, the disclosure of which is incorporated herein by reference. The motion sensor or detector 14 gives a signal having an amplitude depending on the motion intensity as is indicated by the curve of FIG. 2. Thus a more intense, faster or stronger movement gives a higher amplitude than a less intense, slower or weaker movement. The motion detector unit 14 comprises the actual motion sensor 14', which preferably is a simplified embodiment of the sensor disclosed in U.S. Pat. No. 5,183,056 for Björn Dalén et al., the sensor having a lower number of magnet poles. The electrical pulses from the motion sensor 14' can be shaped to a suitable varying electric voltage by a pulse forming procedure. The illustrated motion sensor 14' produces output signals of attenuated oscillation type comprising decaying pulses having some characteristic frequency. For shaping this signal it is provided to a low-pass filter 14" having a very low upper limit frequency of for example 28 Hz. The filtered signal is then amplified by an amplifier 14''' having a suitably chosen gain.

In the motion sensor unit 11 there is also a processor unit, CPU 15, supplemented with additional units such as a read only memory (ROM) 17, a dynamic memory RAM 19 and a timer 21. The motion sensor unit 11 further comprises a comparator 23, a memory 25 for an identification number of the unit, an electrochemical battery 27, and an on/off-switch 29. Finally a radio frequency transmitter 31 is provided. The radio frequency transmitter 31 transmits signals on an antenna 32, for example in the shape of coil of conducting wire having a few turns or piece of straight wire located completely inside the measuring device 11. The various components of the sensor unit 11 are connected by conventional power supply lines and signal lines well understood by those skilled in the art and therefore all of them are not illustrated in the figure.

The comparator 23 receives on one of its input terminals the signal $V_{sense}$ from the detector unit 14 and compares this signal to the voltage $V_{ref}$ received on its other input terminal. The reference voltage $V_{ref}$ is generated by voltage dividing the supply voltage of the electrochemical battery 27. The output signal of the comparator 23 is communicated to the processor 15, for example as an interrupt signal. It has a first level, an activity level, only when the output signal $V_{sense}$ of the detector unit 14 is larger than the reference voltage $V_{ref}$ and otherwise it stays at a second level indicating an inactive state.

The timer circuit 21 is arranged to wake up the processor unit 15 256 times each hour, i.e. at times separated by intervals of approximately 14 seconds. At these wake up times the processor determines whether the output signal $V_{sense}$ of the sensor 14, as compared by the comparator 23, has been larger than a threshold value $V_{ref}$ set as another input signal to the comparator 23, shown by the time diagram of FIG. 2 illustrating the smoothed output from the sensor 14'. As the comparator 23, an operational amplifier may be used in the case where the sensor output signal is small. In any case, a flag is set in the dynamic memory 19 when the sensor output signal $V_{sense}$ exceeds the predetermined threshold value $V_{ref}$.

Also, the wake up timer 21 must be supplied with current permanently. At each 14th second it thus wakes the processing unit 15 which then adds a one to a counter, also arranged inside the dynamic memory 19, in the circumstance where the sensor output signal has set the activity flag in the memory 19. In the opposite circumstance, the counter value is not modified. Then the central processor unit checks if it is time to transmit information. Preferably, this will be done once each hour. If it is time for a transmission, it will start the transmitter 31 and transmit the stored data. Suitable frequencies may be for example 433 MHz and 418 MHz.

The stored data consist of the counted values for the last 24 hours, as shown in FIG. 3. There are thus 24 memory fields 33, each one holding a counted value (for example "185", "205", etc.). There is also an index pointer, stored in a memory field 34 of the RAM memory 19, which points to the counted value memory field 33, which was most recently updated.

In FIG. 4 the format of the transmitted information block is illustrated, starting with a start field 41 telling the receiver that a new data block is coming. Then there is an RF-type field 43 following directly after the start field 41, the contents of this field identifying the type of message or type of transmitter, for instance that this is a message sent from an activity measuring device. After the type field 43, an identity number field 45 follows holding identity information as stored in the identity number storage means 25 and identifying the activity meter. After the identity field 45 there is a field 47 holding the value of the index pointer, as stored in the memory register 34. Field 47 points at the latest updated count memory field 33, this pointer value indicating approximately the hour of the day to which this transmission refers. Then follows the information stored in the memory means as counted value field 49 for the counted values, that is the data stored in all the memory fields 33, and it comprises thus 24 partial fields having each one the length of one byte. The field thus holds information for the last 24 hours in a cyclical pattern, the number of the most recent hour or counted value being indicated by the value of the index pointer, as stored in the field 47. Finally, there is a checksum field 51 following after the counted values field 49. This whole data block is transmitted very rapidly and only once per hour, so that a transmission period of a few hundreds of milliseconds is only required therefor.

Figure 5:
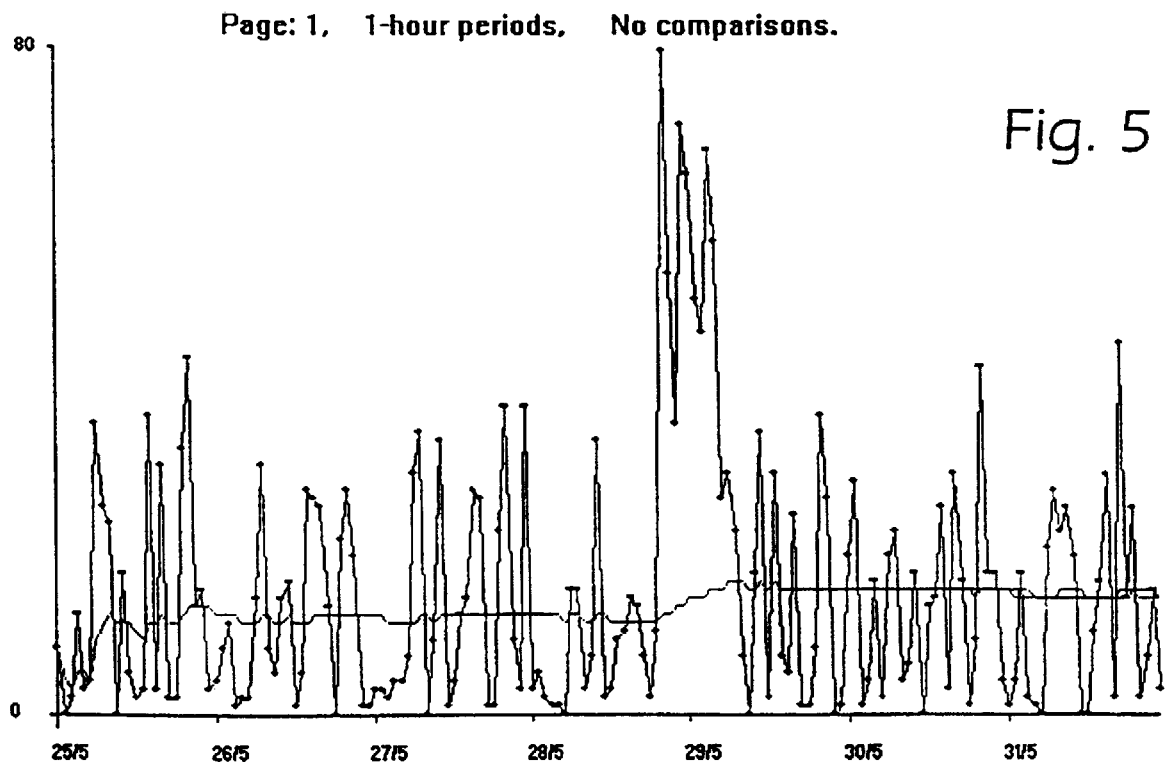
FIG. 5 is a diagram where the counted values are plotted as a function of a time for several consecutive days.

The information transmitted can then be received from the antenna 13 and the transmitted count values are processed in the processor 7. It will store the received counted values to make an evaluation thereof. A typical diagram of counted values as a function of time is plotted in FIG. 5 illustrating the values of one week. Also plotted in this figure is a line illustrating a running mean or average calculated from the count values registered previously to each activity count. The activity is generally low in this example but a peak is obtained about the beginning of the day 29/5. This peak may signal an estrus period.

Figure 7:
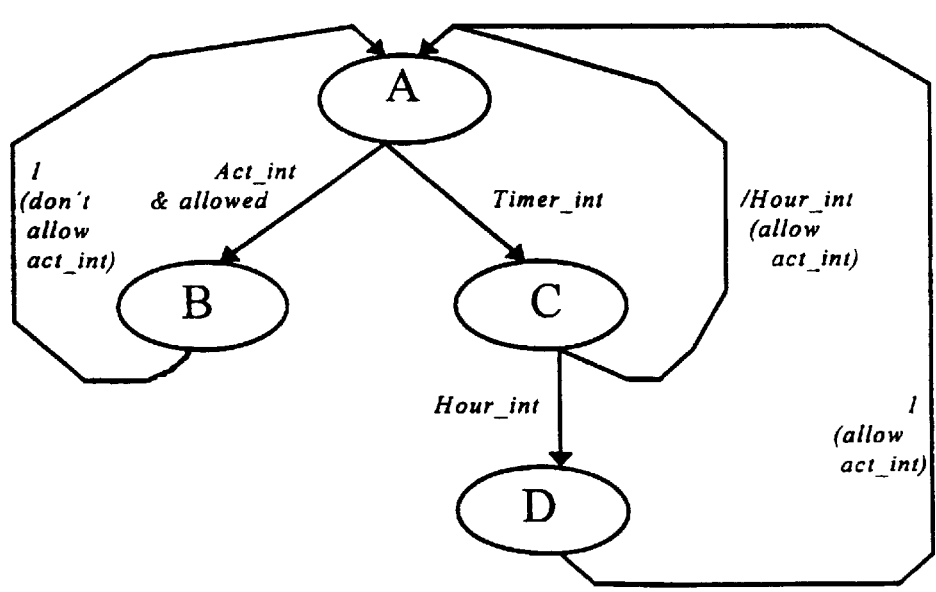
FIG. 7 is a state diagram illustrating the operation of a processor 15 in the activity measuring device.

In FIG. 7 the function of the processor 15 is illustrated by a state diagram. The processor 15 and in particular the CPU thereof can take four states, A, B, C and D.

The CPU will mostly be in state A, the quiescent or idling state. In this state the CPU is idle, just waiting for an interrupt. There are two kinds of interrupt which can wake up the CPU, either an activity interrupt, which is the same as an activity pulse, from the comparator 23 or a timer interrupt from the wake-up timer 21 meaning that a time period of 14 seconds has elapsed.

If there is an activity interrupt or activity pulse when the CPU is in state A and the interrupt is allowed, which means that the activity interrupt is the first one in the present time period of 14 seconds, the processor 7 will proceed to state B. In state B the counter 33 pointed to by the pointer 34 that counts the present activity pulses will be incremented by one step and then a flag is set which tells the processor that no other activity interrupt is allowed within this time period. When finished in state B the processor always go back to state A. If there is a timer interrupt and the current state is A the CPU will go to state C. In state C there will be a check whether one hour has elapsed since a RF transmission took place. If the latest RF transmission occurred less then one hour ago the processor will go back to state A, but before that activity interrupts will be allowed by resetting of the flag which controls this. If one hour has elapsed the next state will be D.

In state D a RF transmission of the transmission block as indicated in FIG. 6, will take place. After the transmission has finished the activity interrupt flag will be reset, allowing activity interrupts to take place, and the processor will go back to state A.

The components of the motion sensor unit 11 which need a permanent current supply comprise the wake up timer 21, the refresh of the dynamic memory 19 and the comparator 23. With a suitable dimensioning of the electronic circuits, a careful selection of voltages etc., the sensor unit 11 can be used for many years without requiring any replacement of the battery 27.

Providing a transmission at periodic times, as described above, also provides other advantages, such as that it may be easily detected that the motion sensor unit 11 is not still operable. Also a low activity of the animal, to which the sensor is attached, can be recognized, such a low activity signalling possibly that the animal is in a bad condition, has some illness, etc. Also the feature of always transmitting the data of the last hours, such as described above the 24 last hours, makes it possible to reconstruct all counted values even in the case where some of the transmissions have not been received.

The on/off switch 29 is necessary since in certain cases it may be required that the motion sensor unit should not emit any radiation, for example when the motion sensor is shipped to a distributor or end user. Also, energy of the electrochemical battery 27 can be saved in those cases where the motion sensor unit is to be stored before actually using it. The switch can preferably be designed as a magnetically operated reed switch, that is a switch that is controlled by an external magnet. Thus, such a switch does not require any mechanical connection to the outside from the interior of the activity meter 11. The activity measuring device can then be very well encapsulated and isolated electrically, without any electrically conductive parts extending from the exterior thereof to the outside, since also the antenna coupled to the transmitter can be totally encapsulated.

Figure 8:
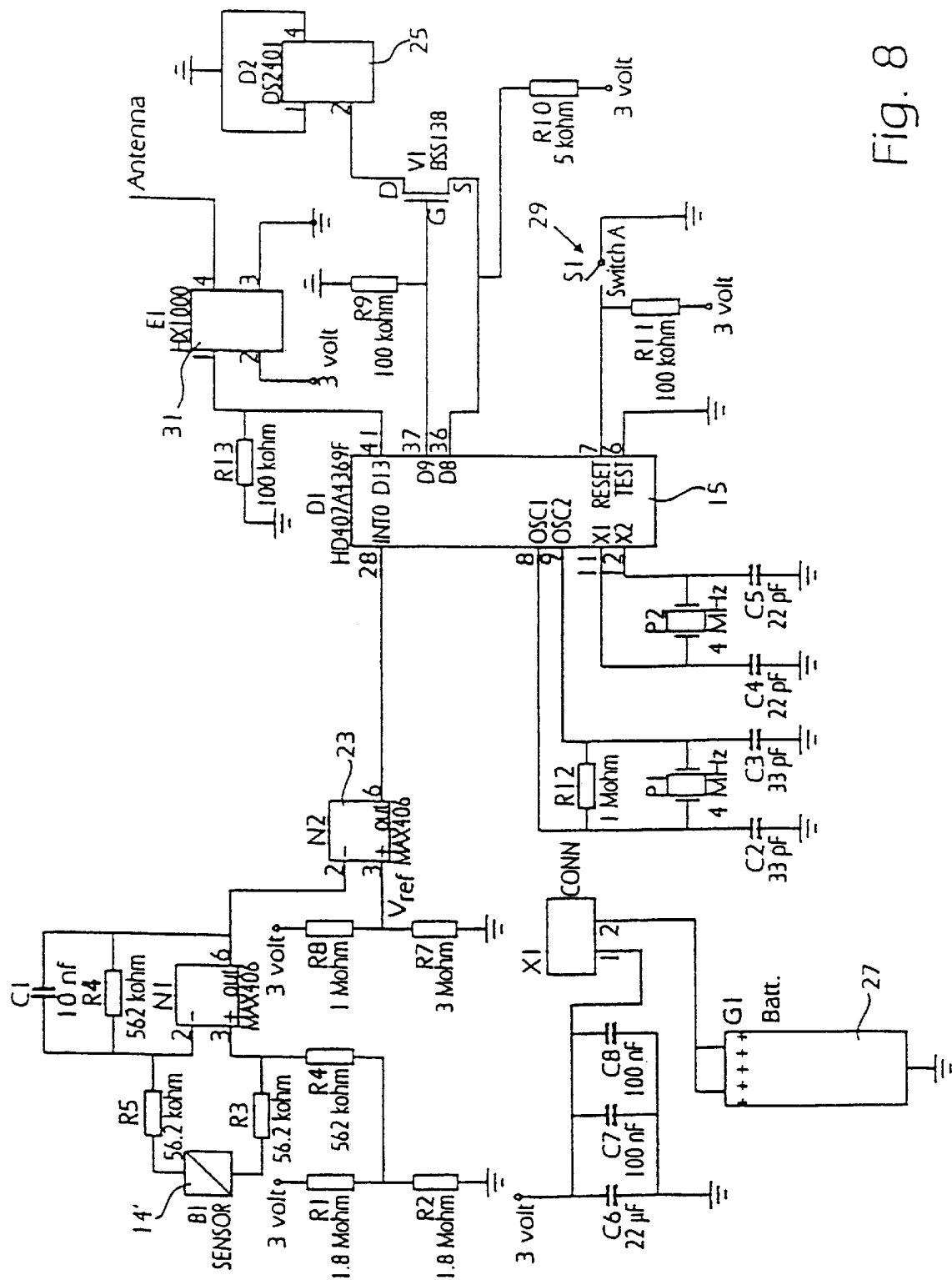
FIG. 8 is a circuit diagram of the activity measuring device.

A circuit diagram of the activity measuring device is shown in FIG. 8. The motion sensor 14' of the kind indicated above provides a signal having alternating polarities between the terminals of the sensor. One of the terminals is then locked to half the voltage of the supply voltage of 3 volts. It is made by connecting one of the terminals to the midpoint of a symmetric voltage divider constructed of two equal resistors R1 and R2. Suitable series resistors R3, R5, R4 connect the terminals of the motion sensor 14' and the midpoint of the voltage divider to the inputs of a differential amplifier N1 that is connected both to act as a lowpass filter and to provide an amplification. This is made by a parallel combination of a capacitor C1 and a resistor R6 connected between that input of amplifier N1, that is not connected to have the potential of 1.5 volts, and the output terminal of the amplifier N1.

This output terminal of the amplifier N1 is also connected to the negative input terminal of a second differential amplifier N2 operating as the comparator 23. The other input terminal, the positive one, of this amplifier N2 is connected to the midpoint of a voltage divider circuit comprising resistors R7 and R8 to provide the voltage reference $V_{ref}$. The other terminals of these resistors, which are not connected to each other at the midpoint, are connected to signal ground and the supply voltage of 3 volts. The output of the amplifier N2 is connected to an interrupt input terminal of the processor D1, 15 of type HD407A4369F that includes suitable ROM- and RAM-memories 17, 19 and a timer circuit 21, as indicated in FIG. 1.

In the stationary processor 7, and in particular when a personal computer 9 is used and connected thereto, the activity counts can be evaluated for finding different states of the considered animal.

The activity measuring installation as described above can be used together with and in a device for separating animals as will be described hereinafter.

In FIG. 6 a corral is shown comprising an area 53 for a herd of freely walking animals. In the following, reference will be made only to cows. It is however obvious that the devices and installations as described herein also can be applied to other animals, for example sheep and goats. The area 53 may for example be a barn or an area provided outdoors, which may be enclosed by a fence. In the area 53 an automatic milking station 55 and a separation device 57 are provided. The automatic milking station 55 comprises a stall 59 having an entrance gate 61, an exit gate 63 and a milking machine 65 that is provided with a robot arm 67 for applying teat cups, not shown, on the teats of a cow present in the stall 59. The milking station 55 also comprises an identification device 69, for identifying a cow entering the milking stall 59 and an examination device 71 for examining the condition of the animal with respect to illness, for example mastitis, blood in the milk, injuries on the udder and the teats. The examination device 71 or an additional examination device may be arranged outside the milking station 55.

The separation device 57 comprises a separation zone 73 which is enclosed by an enclosure 75, for example a fence. In the separation zone 73 any kind of treatment may be performed on the cow which has been separated. The treatment might be any medical treatment, for example curing a disease by an injection. It might also be insemination or manual milking in the case that the automatic milking did not succeed. Finally it might be applying an earmark or even that the cow should be separated to be brought to slaughterhouse. In the enclosure 75 there are provided three entrance devices 77 and an exit gate 79 in particular manually operated but may alternatively be automatically operated, to permit removal of a cow from the separation zone 73. The entrance devices 77 are forming animal passages 81 leading from the area 53 to the separation zone 73. It should however be noted that more or less such entrance devices 77 might be provided. Each entrance device comprises a stall 77 having a front gate 83 and a rear gate 85. In each stall 77 there is provided a feeding device 87. Preferably the feeding device 87 is of the type which offers the cows concentrate to eat. Such feed is particularly attractive to the cows and therefore they frequently visit such feeding stalls. Moreover, when entering the stall 77 for eating concentrate, the cows need only to be present in the stall 77 for a short period of time in comparison to the circumstance when they eat ensilage that may continue for a long period of time. Furthermore an identification device 89 is provided at each entrance device for identifying a cow entering the stall 77.

The entrance and exit gates 61, 63, the automatic milking machine 65, the identification device 69, the examination device 71, the front gates 83, the rear gates 85, the feeding devices 87 and the identification devices 89 are controlled by the control and evaluation processor 7 of FIG. 1.

The arrangement described above functions as follows. Voluntarily a cow which needs to be milked enters the milking station 55. There she is identified by the identification device 69, undergoes a condition examination by the examination device 71 and is milked by the automatic milking machine 65. The condition examination may be performed by optical means, not shown, to detect an external injury on the udder and the teats or that the udder and the teats are not clean. The condition examination may also be performed by measurements on the milk, in regard of for example conductivity or temperature for detecting diseased cows. Furthermore it is possible to measure the presence and the quantity of various kinds microbes in the milk.

The result of the examination is stored and processed by the control processor 7. If the result does not indicate any defects the milk is delivered and the cow leaves the milking station 55 through the exit gate 63 and enters the area 53. On the other hand, if the result indicates a disease or some other defect the milk is transported to a waste tank, not shown, and the cow is allowed to leave the milking station 55 through the exit gate 63 and enters the area 53. Furthermore if the robot arm 67 of the milking machine 65 does not succeed in bringing the teat cups on the teats the exit gate 63 is opened 50 so that the cow can leave the milking station 55 and enter the area 53. In the area 53, the cow is allowed to walk around freely and will after a while enter one of the feeding stalls 77. If the examination result indicates that a specific cow should be separated due to any of the defects mentioned above, or due to the fact that a low activity of the cow has been detected by the motion sensor unit 11 of FIG. 1 and this fact has been communicated to the stationary control processor 7, or that the cow should be inseminated because of high activity etc., the rear gate 85 will be closed when this specific cow has entered the stall 77 and is identified by the identification device 89. In the stall 77 the cow can be offered feed through the feeding device 87. However the front gate 83 is opened as commanded by the control processor 7, that is not visible in FIG. 6 but, as has been already said, is supposed to control the various devices of the corral installation through suitable control lines or control channels, not shown. Thus the cow has to enter the separation zone 73. Thereafter the front gate 83 is closed and any treatment could be performed on the cow so separated. After the treatment the cow can be removed to the area 53 through the exit gate 79.

For the cows which should not be separated the stalls 77 are functioning as normal feeding stalls, i.e. cows entering the stalls 77 for eating can after the eating has finished leave the stalls 77 in the backward direction, through the rear gates 85. Advantageously all of the feeding stalls 77 in the area 53 form passages 81 lead to the separation zone 73, since in this case the cows cannot avoid a feeding stall in which they can be separated.

What is claimed is:

1. A method of monitoring the motion intensity of a domestic animal, the animal being provided with sensor means for different motion states including a first, normal state and a second, particular state, and a transmitter operatively connected to the sensor means, comprising the steps of:

determining by the sensor means, at periodically repeated times having time intervals therebetween of a first predetermined length, whether the animal during a next time interval has adopted the second, particular state and upon determining that the animal has adopted the second, particular state, counting the number of the first times; and transmitting from the transmitter, at periodically repeated times occurring less frequent than the first time and having time intervals therebetween of a second predetermined length that is greater than the first predetermined length, information to an evaluation station, the transmitted information including the counted number of the first times corresponding to how many times after at least one previous transmission that the second, particular state has been adopted.

2. A method according to claim 1, wherein at the periodically repeated times, when the information is transmitted to the evaluation station, the information also includes the counted number of the first times corresponding to how many times the second, particular state has been adopted during a plurality of prior second time intervals.

3. A method according to claim 1, wherein at the paretically repeated times, when information is transmitted to the evaluation station, the information also includes identification information for identifying the transmitter, the sensor means and the animal wearing the sensor means, and the transmitter means.

4. A device for monitoring the motion intensity of a domestic animal, comprising:

sensor means attached to the animal for sensing different motion states of the animal, the motion states including at least a first, normal state and a second, particular state;

transmission means for transmitting information to an evaluation station and operatively connected to the sensor means;

timer means for providing first clock pulses of a first predetermined rate, the first clock pulses having first time intervals therebetween of a first predetermined length;

memory means for storing at least one counted number;

determining means coupled to the sensor means and the timer means for receiving the first clock pulses and for determining, at the reception of each first clock pulse, whether the animal during the first time interval from the next previous time when a first clock pulse was received, has adopted the second, particular state, the determining means also being operatively coupled to the memory for storing therein the number of such first times, when the second, particular state has been adopted; and control means coupled to the memory means, the timer means and the transmission means for transmitting, at periodically repeated times less frequent than the first times and having second time intervals therebetween of a second predetermined length larger than the first predetermined length, information to the evaluation station including the counted number stored in the memory means.

5. A device according to claim 4, wherein, the memory means are arranged for storing a plurality of the counted numbers, the determining means being arranged for storing the counted numbers for at least two successive second time intervals the second predetermined length, and the control means are arranged for transmitting, at the periodically repeated second times when the information is transmitted to the evaluation station, information including the counted numbers during a plurality of prior second time intervals having the second length.

6. A device according to claim 4, wherein, the memory means are arranged for storing an identification sequence, and the control means are arranged to transmit to the evaluation station identification information derived from the stored identification sequence for identifying the transmitter and thereby the sensor means and the animal at the periodically repeated second times.

* * * * *